United States Patent
Xiao et al.

(10) Patent No.: US 9,788,725 B2
(45) Date of Patent: Oct. 17, 2017

(54) MEDICAL IMAGE DISPLAY APPARATUS AND METHOD

(71) Applicant: Toshiba Medical Systems Corporation, Otawara-shi (JP)

(72) Inventors: Qilin Xiao, Beijing (CN); Yong Sun, Beijing (CN); Zengzi Zhang, Beijing (CN); Zhiliang Zhang, Beijing (CN); Yufei Li, Beijing (CN)

(73) Assignee: Toshiba Medical Systems Corporation, Otawara-shi (JP)

(*) Notice: Subject to any disclaimer, the term of this patent is extended or adjusted under 35 U.S.C. 154(b) by 336 days.

(21) Appl. No.: 13/936,397

(22) Filed: Jul. 8, 2013

(65) Prior Publication Data
US 2014/0015856 A1    Jan. 16, 2014

(30) Foreign Application Priority Data

Jul. 11, 2012 (CN) .......................... 2012 1 0240590

(51) Int. Cl.
*G09G 5/30* (2006.01)
*A61B 5/00* (2006.01)
(Continued)

(52) U.S. Cl.
CPC ............ *A61B 5/0033* (2013.01); *G06T 11/00* (2013.01); *G06T 19/00* (2013.01); *A61B 6/5235* (2013.01);
(Continued)

(58) Field of Classification Search
CPC .................................................. A61B 6/463
(Continued)

(56) References Cited

U.S. PATENT DOCUMENTS 5,810,007 A * 9/1998 Holupka et al. ............... 600/439
6,466,224 B1 * 10/2002 Nagata et al. ................. 345/592
(Continued)

FOREIGN PATENT DOCUMENTS

| CN | 1349718 A | 5/2002 |
| CN | 101893980 A | 11/2010 |

(Continued)

OTHER PUBLICATIONS

Image fusion algorithm based on regional variance and multi-wavelet bases Hua Tian; Ya-nan Fu; Pei-Guang Wang Future Computer and Communication (ICFCC), 2010 2nd International Conference on Year: 2010, vol. 2 pp. V2-792-V2-795, DOI: 10.1109/ICFCC.2010.5497628.*

(Continued)

*Primary Examiner* — Javid A Amini
(74) *Attorney, Agent, or Firm* — Oblon, McClelland, Maier & Neustadt, L.L.P.

(57) ABSTRACT

The present invention discloses a medical image fusion apparatus and method. The medical image fusion apparatus comprises: a display unit configured to display a plurality of medical images in layers in one window on a screen, wherein the arrangement direction of the plurality of medical images is different from the extension direction of the plane on which each medical image exists; an operation detection unit configured to detect an operation of selecting the medical images to be fused from the plurality of medical images; and a fused image generation unit configured to generate a fused image of the medical images to be fused according to the selection operation, wherein the display unit is further configured to display the fused image in a predetermined region in the window.

16 Claims, 9 Drawing Sheets

(51) Int. Cl.
*G06T 19/00* (2011.01)
*G06T 11/00* (2006.01)
*A61B 6/00* (2006.01)

(52) U.S. Cl.
CPC .... *G06T 2210/41* (2013.01); *G06T 2219/028* (2013.01)

(58) Field of Classification Search
USPC .......................................................... 345/629
See application file for complete search history.

(56) References Cited

U.S. PATENT DOCUMENTS

| | | | | |
|---|---|---|---|---|
| 2002/0015536 | A1* | 2/2002 | Warren | G06T 5/50 382/284 |
| 2003/0154201 | A1* | 8/2003 | Berestov | G06T 17/05 |
| 2007/0100225 | A1* | 5/2007 | Maschke | A61B 6/032 600/407 |
| 2008/0262312 | A1* | 10/2008 | Carroll | A61B 1/00009 600/160 |
| 2009/0036902 | A1* | 2/2009 | DiMaio | A61B 19/2203 606/130 |
| 2009/0213034 | A1* | 8/2009 | Wu | G06F 19/321 345/1.1 |
| 2009/0296989 | A1* | 12/2009 | Ramesh et al. | 382/103 |
| 2010/0014780 | A1* | 1/2010 | Kalayeh | G06T 1/00 382/284 |
| 2010/0069758 | A1* | 3/2010 | Barnes | A61B 5/0059 600/473 |
| 2010/0207936 | A1* | 8/2010 | Minear et al. | 345/419 |
| 2010/0231705 | A1* | 9/2010 | Yahav et al. | 348/115 |
| 2011/0001052 | A1* | 1/2011 | Struye | G01T 1/2014 250/369 |
| 2011/0007954 | A1* | 1/2011 | Suehling | G06K 9/00362 382/128 |
| 2011/0038517 | A1* | 2/2011 | Mistretta | A61B 6/02 382/128 |
| 2011/0040169 | A1* | 2/2011 | Kamen | A61B 6/037 600/411 |
| 2011/0064327 | A1* | 3/2011 | Dagher | G06T 5/004 382/263 |
| 2011/0069063 | A1* | 3/2011 | Liao | A61B 90/37 345/419 |
| 2011/0081296 | A1* | 4/2011 | Barr | A01K 67/0336 424/9.2 |
| 2011/0125011 | A1* | 5/2011 | Wieczorek | A61B 6/032 600/427 |
| 2011/0145693 | A1* | 6/2011 | Mutic | G06F 19/321 715/233 |
| 2011/0158491 | A1* | 6/2011 | Markova | G06T 3/0081 382/128 |
| 2012/0014574 | A1* | 1/2012 | Ferschel | G06T 7/0012 382/128 |
| 2012/0019548 | A1* | 1/2012 | Zhu | G06T 11/001 345/589 |
| 2012/0038649 | A1* | 2/2012 | Kanitsar | G06T 11/003 345/440 |
| 2012/0093383 | A1* | 4/2012 | Claus | A61B 6/032 382/131 |
| 2012/0184642 | A1* | 7/2012 | Bartling | A61B 5/0515 523/113 |
| 2012/0209108 | A1* | 8/2012 | Qian | A61B 6/032 600/425 |
| 2012/0256920 | A1* | 10/2012 | Marshall et al. | 345/420 |
| 2012/0308115 | A1* | 12/2012 | Sun | H04N 13/026 382/154 |
| 2013/0135287 | A1* | 5/2013 | McCabe | A61B 6/466 345/419 |
| 2013/0172731 | A1* | 7/2013 | Gole | A61B 5/0035 600/424 |
| 2013/0172739 | A1* | 7/2013 | Paladini | A61B 6/4258 600/436 |
| 2013/0218024 | A1* | 8/2013 | Boctor | A61B 34/20 600/476 |
| 2013/0261446 | A1* | 10/2013 | Paladini | A61B 5/0064 600/436 |
| 2014/0003700 | A1* | 1/2014 | Hermosillo Valadez | G06T 11/003 382/131 |
| 2014/0328531 | A1* | 11/2014 | Lee | H04N 13/0275 382/131 |
| 2014/0354642 | A1* | 12/2014 | Wiemker | G06T 5/50 345/424 |
| 2015/0003708 | A1* | 1/2015 | Prevrhal | G06T 11/008 382/131 |
| 2015/0031990 | A1* | 1/2015 | Boctor | A61B 34/20 600/424 |

FOREIGN PATENT DOCUMENTS

| | | | |
|---|---|---|---|
| CN | 102292747 | A | 12/2011 |
| EP | 1923838 | A1 * | 5/2008 |
| JP | 2000-105279 | | 4/2000 |
| JP | 1349718 | A | 5/2002 |
| JP | 2006-53102 | | 2/2006 |
| JP | 2007-144175 | | 6/2007 |
| JP | 2007-282656 | | 11/2007 |
| JP | 2009-95671 | | 5/2009 |
| JP | 4737264 | B2 | 7/2011 |
| WO | WO 00/70881 | A1 | 11/2000 |

OTHER PUBLICATIONS

A Novel Medical Image Fusion Scheme Using Weighted Sum of Multi-scale Fusion Results Afzal, S.; Majid, A.; Kausar, N. Frontiers of Information Technology (FIT), 2013 11th International Conference on Year: 2013 pp. 113-118, DOI: 10.1109/FIT.2013.28.*

Evolutionary algorithm based automated medical image fusion technique: Comparative study with fuzzy fusion approach Das, A.; Bhattacharya, M. Nature & Biologically Inspired Computing, 2009. NaBIC 2009. World Congress on Year: 2009 pp. 269-274, DOI: 10.1109/NABIC.2009.5393715.*

A novel approach of image fusion on MR and CT images using wavelet transforms Sekhar, A.S.; Giri Prasad, M.N. lectronics Computer Technology (ICECT), 2011 3rd International Conference on Year: 2011, vol. 4 pp. 172-176, DOI: 10.1109/ICECTECH.2011.5941881.*

Multimodal medical image fusion based on Integer Wavelet Transform and Neuro-Fuzzy Kavitha, C.T.; Chellamuthu, C. Signal and Image Processing (ICSIP), 2010 International Conference on Year: 2010 pp. 296-300, DOI: 10.1109/ICSIP.2010.5697486.*

Image Fusion: Principles, Methods, and Applications Tutorial EUSIPCO 2007, Jan Flusser et al, 2007.*

Combined Office Action and Search Report dated Oct. 29, 2015 in Chinese Patent Application No. 201210240590.6 (with English language translation).

Combined Chinese Office Action and Search Report dated Jul. 22, 2016 in Patent Application No. 201210240590.6 (with English translation of categories of cited documents).

* cited by examiner

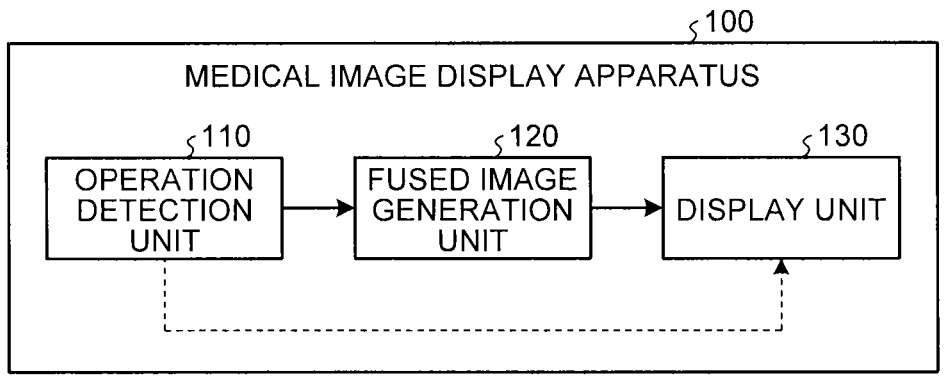
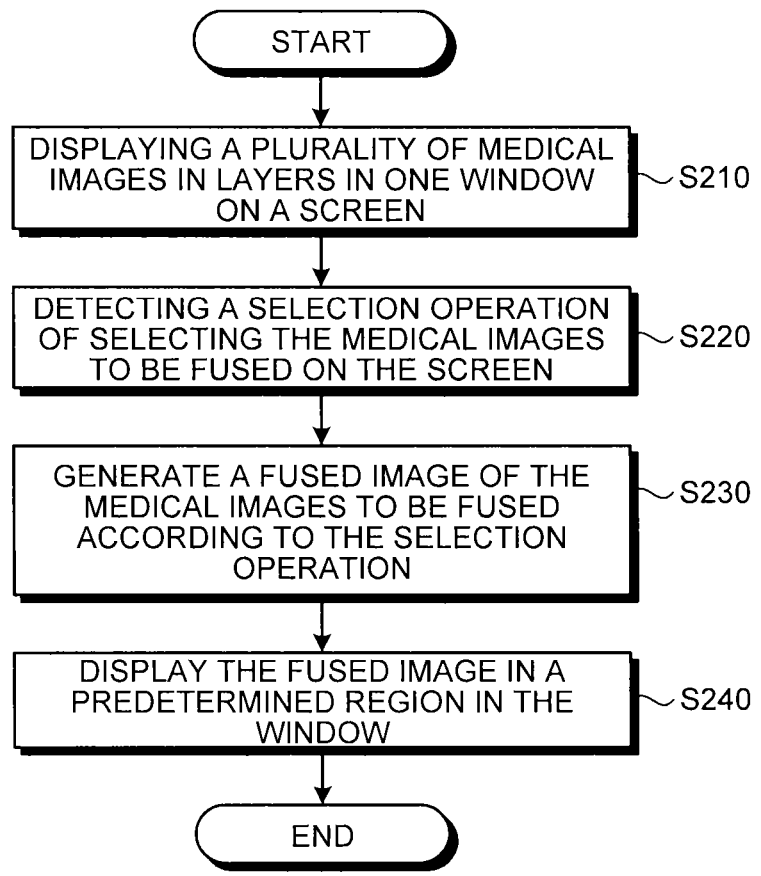

MEDICAL IMAGE DISPLAY APPARATUS AND METHOD

CROSS-REFERENCE TO RELATED APPLICATIONS

This application is based upon and claims the benefit of priority from Chinese Patent Application No. 201210240590.6, filed on Jul. 11, 2012, the entire contents of which are incorporated herein by reference.

FIELD

The present invention relates to the field of computer vision, and more particularly to a medical image display apparatus and method.

BACKGROUND

Image fusion has been widely used in medical field in recent years. Image fusion refers to a technology of combining two or more images of different information types into one image to acquire more information. In the fusion of medical images, the combination mode of medical images varies according to different observation purposes. For instance, images acquired from different imaging devices (also referred to images of different modalities) or images of different sequences acquired from the same imaging device are fused. A sequence refers to a plurality of parallel images that are acquired by an imaging device from different positions of an imaged object at substantially the same moment, and the image corresponding to each position is referred to as a slice. Therefore, how to manage various medical images in a fusion device effectively becomes more and more important.

In some existing fusion devices, each image input to be fused and a fused image respectively occupy a window on a display screen, leading to that display window resource is in shortage when there are a plurality of input images to be fused or a plurality of fused images are needed.

In other existing fusion devices, a plurality of input images are arranged in a thumbnail form and only one image can be operated at one moment. After switching to an input image, the operation on the former input image cannot be kept.

BRIEF DESCRIPTION OF THE DRAWINGS

FIG. 1 illustrates a schematic block diagram of a medical image display apparatus according to an embodiment of the present invention;

FIG. 2 illustrates a schematic flowchart of a medical image fusion method according to an embodiment of the present invention;

DETAILED DESCRIPTION

Figure 3A:
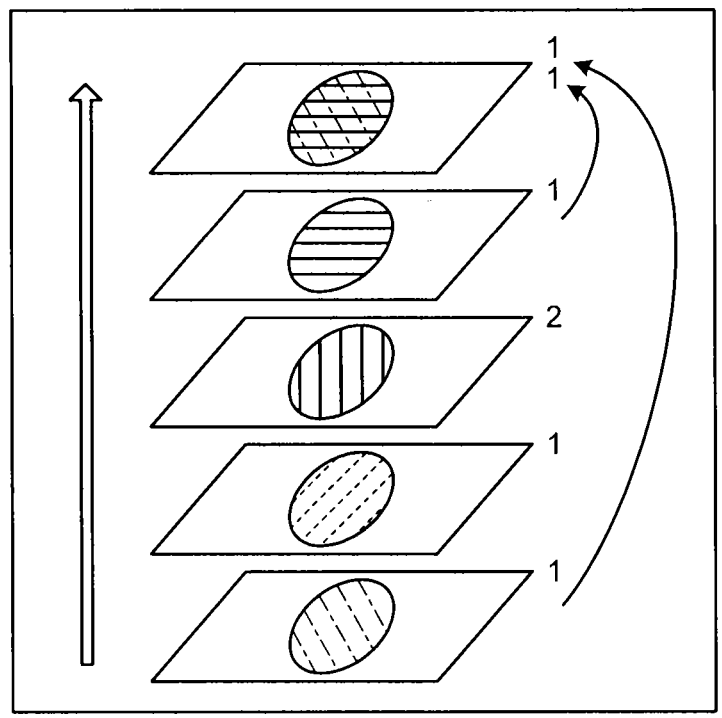
FIGS. 3a-3c illustrate schematic diagrams of a fusion window according to embodiments of the present invention.

A simplified summary of the present invention is predetermined below to provide a basic understanding of some aspects of the present invention. It should be understood that the summary, which is not an exhaustive overview of the present invention, is not intended to identify the key or critical parts of the present invention or limit the scope of the present invention, but merely to present some concepts in a simplified form as a prelude to the more detailed description that is discussed later.

In accordance with an aspect of the present invention, there is provided a medical image display apparatus, comprising: a display unit configured to display a plurality of medical images in layers in one window on a screen, wherein the arrangement direction of the plurality of medical images is different from the extension direction of the plane on which each medical image exists; an operation detection unit configured to detect a selection operation of selecting the medical images to be fused from the plurality of medical images; and a fused image generation unit configured to generate a fused image of the medical images to be fused according to the selection operation, wherein the display unit is further configured to display the fused image in a predetermined region in the window.

In accordance with another aspect of the present invention, there is provided a medical image fusion method, comprising: displaying a plurality of medical images in layers in one window on a screen, wherein the arrangement direction of the plurality of medical images is different from the extension direction of the plane on which each medical image exists; detecting a selection operation of selecting the medical images to be fused from the plurality of medical images; generating a fused image of the medical images to be fused according to the selection operation; and displaying the fused image in a predetermined region in the window.

Further, in accordance with still another aspect of the present invention, there is provided a computer program for realizing the aforementioned method.

Additionally, in accordance with still further aspect of the present invention, there is provided a computer program product in the form of a medium at least readable to a computer, on which computer program codes are recorded to realize the aforementioned method.

The present invention will be better understood by reference to the following description taken in conjunction with accompanying drawings in which identical or like sections are designated with identical or like reference signs designate. The accompanying drawings, together with the detailed description below, are incorporated into and form a part of the specification, and serve to further illustrate, by way of example, preferred embodiments of the present invention and to explain the principle and advantages of the present invention. In the accompanying drawings:

Embodiments of the present invention are described below with reference to the accompanying drawings. The elements and features described in a figure or an embodiment of the present invention can be combined with the elements and features shown in one or more other figures or embodiments. It should be noted that, for the purpose of clarity, representations and descriptions of elements and processes which are known to those skilled in the art or are not related to the present invention, are not presented in the drawings and the description.

FIG. 1 illustrates a schematic block diagram of a medical image display apparatus according to an embodiment of the present invention. As shown in FIG. 1, a medical image display apparatus 100 includes an operation detection unit 110, a fused image generation unit 120 and a display unit 130. The display unit 130 is configured to display a plurality of medical images in layers in one window on a screen, wherein the arrangement direction (or the layering direction) of the plurality of medical images is different from the extension direction of the plane on which each medical image exists. The screen may be a screen of any appropriate display device, such as a screen of a display or touch panel. The operation detection unit 110 is configured to detect, on the screen, a selection operation of selecting the medical images to be fused from the plurality of medical images. The fused image generation unit 120 is configured to generate a fused image of the medical images to be fused according to the selection operation detected by the operation detection unit 110. The display unit 130 is further configured to display the generated fused image in a predetermined region in the window.

It should be understood that the plurality of medical images displayed by the display unit are medical images subjected to a registration. The plurality of medical images may be registered before being input to the medical image display apparatus 100. Alternatively, the medical image display apparatus 100 may also include a registration unit for registering the plurality of medical images. The registration of the medical images is not described herein in detail so as not to obscure the present invention unnecessarily.

The dotted line connection between the operation detection unit 110 and the display unit 130 shown in FIG. 1 indicates that in some other embodiments of the present invention, the display unit 130 may change/display/hide the display of corresponding medical images or the fused image according to a predetermined operation detected by the operation detection unit 110. This connection relationship is optional but not necessary, and will be discussed later.

Figure 3B:
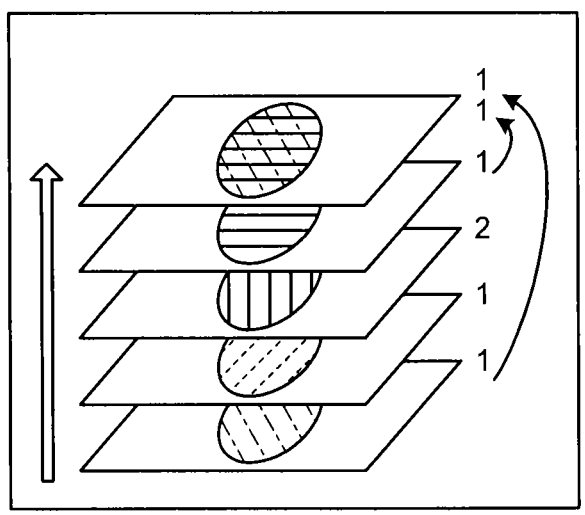
Figure 3C:
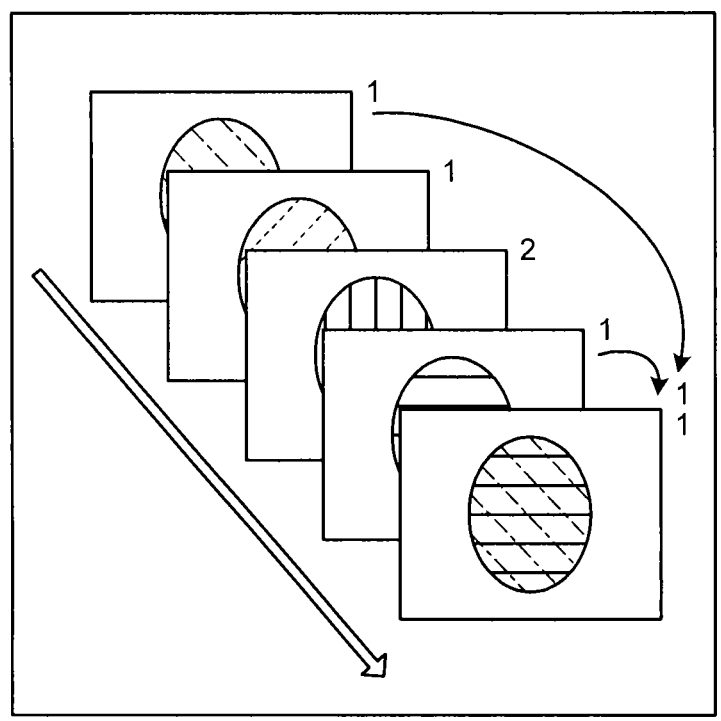

For facilitating understanding the present invention, FIG. 3a to FIG. 3c show schematic diagrams of a fusion window according to embodiments of the present invention.

In FIG. 3a, the four images in the lower part of the window are schematic diagrams of four medical images displayed in layers. The arrangement direction of the medical images is different from the extension direction of the plane on which each medical image exists. In FIG. 3a, the arrangement direction (as indicated by the hollow arrow) of the medical images is substantially vertical to the extension direction of the plane on which each medical image exists. In FIG. 3a, a fused image is displayed on the top of the window and located in a layer above the uppermost layer of medical image. The fused image is formed by fusing two medical images selected from the four medical images (as indicated by the solid arrow).

In FIG. 3b, the four images in the lower part of the window are schematic diagrams of four medical images displayed in layer. The arrangement direction (as indicated by the hollow arrow) of the medical images, which is different from the extension direction of the plane on which each medical image exists, is also substantially vertical to the extension direction of the plane on which each medical image exists. In this figure, the fused image, which is displayed on the top of the window and located in a layer above the uppermost layer of medical image, is formed by fusing two medical images selected from the four medical images (as indicated by the solid arrow).

In FIG. 3c, the four images in the left upper part of the window are schematic diagrams of four medical images displayed in layers. The arrangement direction (as indicated by the hollow arrow) of the medical images is different from the extension direction of the plane on which each medical image exists. In this example, the arrangement direction of the medical images is intersected with the plane on which each medical image exists. A fused image is displayed in the right lower part of the window, located outside the rightmost medical image, and is formed by fusing two medical images selected from the four medical images (as indicated by the solid arrow).

As an example of a fusion window, the display of the medical images and the fused image shown in FIG. 3a to FIG. 3c is merely for illustrating but not for limitation, a case in which a plurality of medical images are displayed in layers in a window on the screen, wherein the arrangement direction of the plurality of medical images is different from the extension direction of the plane on which each medical image exists, and the fused image is displayed in a predetermined region in the window. Based on the description and diagrams above, those skilled in the art may devise more other display forms of the medical images and the fused image which follow the concept of the present invention. For instance, some of the plurality of medical images may be overlapped, or the fused image is displayed at another position in the window, which will not be listed here one by one.

In an embodiment of the present invention, the display unit 130 may display the plurality of medical images and the fused image as two-dimensional images, as shown in FIG. 3c. For instance, the display unit 130 may display the medical images in layers by setting the positions of the medical images in the window and display the fused image in a predetermined region by setting the position of the fused image in the predetermined region. The display of two-dimensional images occupies less system resource.

In another embodiment of the present invention, the display unit 130 may display the plurality of medical images and the fused image as three-dimensional images, as shown in FIGS. 3a-3b. For instance, the display unit 130 may perform a three-dimensional rendering on the plurality of medical images using an existing appropriate method to form a three-dimensional volume and display the three-dimensional volume in the window, and perform a three-dimensional rendering on the fused image using an existing appropriate method and display the fused image subjected to the three-dimensional rendering at a predetermined position in the window, and preferably on the three-dimensional volume of the plurality of medical images. By displaying the medical images and the fused image as three-dimensional images, the user can view each image more intuitively, especially when the input medical images are associated with each other in space relationship. Here, only FIG. 3a and FIG. 3b are taken as examples of three-dimensional rendering. However, it is apparent that what is shown in FIG. 3c may be a two-dimensional display, or a three-dimensional rendering may be implemented on the basis of what is shown in FIG. 3c.

Ideally, each layer of medical image is not overlapped and can be wholly presented, as shown in FIG. 3a. However, if there are a great many medical images input, the medical images in adjacent layers may be partially overlapped, as shown in FIG. 3b and FIG. 3c, so that the window space occupied by the medical images can be further saved to display more medical images in one window. Medical images in different layers may be parallel to each other. In addition, the fused image may be parallel to each layer of medical image.

For facilitating observation and operation, the predetermined region for the display of the fused image may be set outside the outermost layer of medical image of the medical images, as shown in FIG. 3a to FIG. 3c. It should be understood that the predetermined region may also be set at any other position in the window that can be observed by the user conveniently.

The plurality of medical images to be fused may include medical images of different modalities and/or different sequences. For facilitating observation, in a preferred embodiment of the present invention, the display unit 130 may distinguish, in the window, the medical images of different modalities with a first kind of identifiers and distinguish the medical images of difference sequences with a second kind of identifiers. Besides, the display unit 130 may further identify the fused image using a combination of the identifiers of the medical images to be fused.

As an example but not a limitation, the medical images of different modalities are distinguished from each other with different border colors, and the medical images of the same modality in different sequences are distinguished from each other with different sequence numbers. For instance, in FIG. 3a to FIG. 3c, the medical images filled with solid lines (horizontal lines or vertical lines) are medical images of the same modality in different sequences, and have the same border color (not shown) and different sequence numbers 1 and 2. The medical images filled with dotted lines (left slashes) and the medical images filled with dash-dotted lines (right slashes) are medical images which have different modalities and thus have different border colors (not shown) from the medical images filled with solid lines. In addition, in each of FIG. 3a to FIG. 3c, the border color of the fused image may be the mixed color (not shown) of the border colors of the medical images to be fused, and the sequence number of the fused image may be the combination of the sequence numbers of the medical images participating in the fusion. Based on the description above, those skilled in the art may devise more other identifiers to identify the medical images of different modalities and the medical images of different sequences, which will not be listed here one by one.

The operations detected by the operation detection unit 110 and corresponding processing are described below in combination with FIGS. 3a-3c and FIG. 4-FIG. 11.

A predetermined selection operation may be used to select the medical images to be fused from a plurality of medical images and to associate the medical images to be fused with a predetermined region in the window. As an example of the selection operation, the medical images (or the copies thereof) may be dragged into the predetermined region, as shown in FIGS. 3a-3c. As another example of the selection operation, the medical images to be fused may be clicked a predetermined times (for example, double click) and then the predetermined region may be clicked (for example, single click) to associate the medical images to be fused with the predetermined region to indicate that the medical images (or the copies thereof) to be fused are to be put in the predetermined region. The selection operation described above may be achieved by manipulating the cursor on a screen with a mouse or through a slide or click on a touch screen by a finger. The operation detection unit 110 may detect the selection operation on the screen using any appropriate existing technology, which will not be described in detail here.

The fused image generation unit 120 fuses the selected medical images according to the selection operation detected by the operation detection unit 110 to generate a fused image. The fused image generation unit 120 may fuse the medical images using any existing appropriate fusion method, which will not be described in detail here.

In addition, in some fusion methods, the overlapping order of the images participating in a fusion has an influence on the effect of the fusion. For instance, according to different fusion algorithms, the pixels of the medical images participating later may cover those of the medical images participating earlier, or vice verse. Thus, in an embodiment of the present invention, the fused image generation unit 120 overlaps the medical images to be fused according to the selection order of the selection operation to generate the fused image. For instance, the medical image selected earlier participates in the fusion before the one selected later, or the fusion may be implemented in a reversed order.

Figure 4:
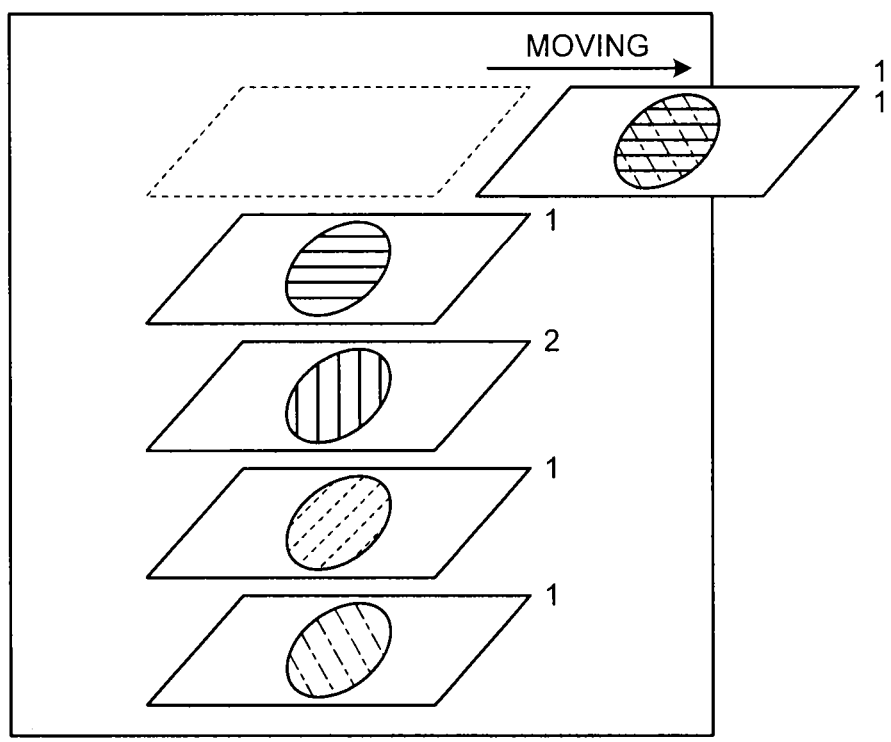
FIG. 4 illustrates a schematic diagram of a fusion cancelling operation according to an embodiment of the present invention.

When to cancel the fusion, the operation detection unit 110 may detect a fusion cancelling operation, and the display unit 130 may cancel the display of the fused image according to the fusion cancelling operation. As an example of the fusion cancelling operation, the fused image may be moved out of the predetermined region, as shown in FIG. 4. As another example of the fusion cancelling operation, the fused image may be clicked a predetermined times (for example, double click). The fusion cancelling operation described above may be achieved by manipulating the cursor on a screen with a mouse or through a slide or click on a touch screen with a finger. The operation detection unit 110 may detect the fusion cancelling operation on the screen using any appropriate existing technology, which will not be described in detail here.

In the aforementioned example in which the medical images of different modalities are distinguished from each other with border colors and the medical images of different sequences are distinguished from each other with sequence numbers, the operation on the medical images and the fused image may also be achieved by operating the sequence numbers of the corresponding images. For instance, the selection operation may associate the medical images to be fused with the predetermined region by operating, for example, dragging or clicking, the sequence numbers of the medical images to be fused. Correspondingly, the fusion cancelling operation may also be achieved by operating the sequence number of the fused image, for example, by dragging the sequence number of the fused image to move the fused image out of the predetermined region.

Figure 5:
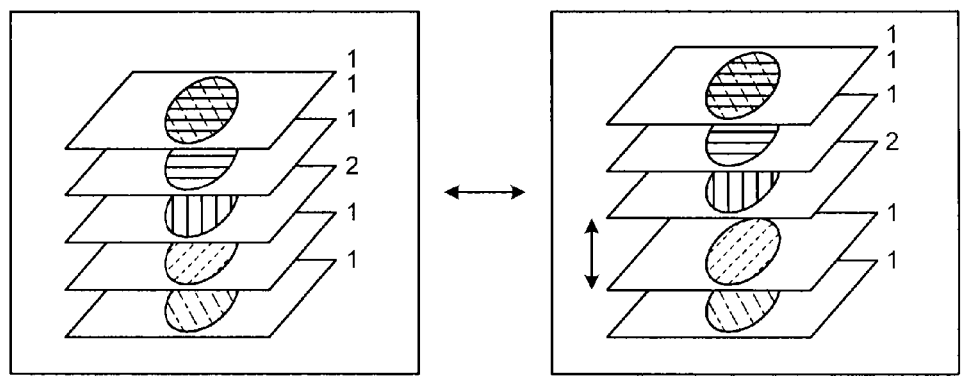
FIG. 5 illustrates a schematic diagram of a layer interval changing operation according to an embodiment of the present invention.

The operation detection unit 110 may further detect a layer interval changing operation, and the display unit 130 may display in the window the layers of images of which two or more layers are changed in layer interval in a window according to the layer interval changing operation. FIG. 5 illustrates a schematic diagram of a layer interval changing operation according to an embodiment of the present invention. In FIG. 5, in the left figure part, a layer interval changing operation is performed on the second and third lowest layers of images in the window, and in the layers of images shown in the window in the right figure part, the layer interval between the second and third lowest layers of images are changed. As an example of the layer interval changing operation, a layer of image may be dragged upwards or downwards to change the interval between the layer of image and an adjacent layer of image. As another example of the layer interval changing operation, the interval between the two layers of images may be changed by a predetermined degree by clicking a position between the two layers of images by a predetermined times (e.g. double click). With the layer interval changing operation, the user can clearly check a region of interest (ROI) in an image, especially when the ROI in the image is sheltered by an image in an adjacent layer. The layer interval changing operation may change, at a time, the interval between two adjacent layers of images, or the intervals between each two of the plurality of layers of images. For instance, a plurality of images may be selected synchronously, for instance, corresponding regions, for example, sides or corners, of the plurality of layers of images may be framed by a box, or corresponding sequence numbers of the plurality of layers of images may be framed by a box, and then the box is stretched to increase the distances between the plurality of layers of images.

Figure 6:
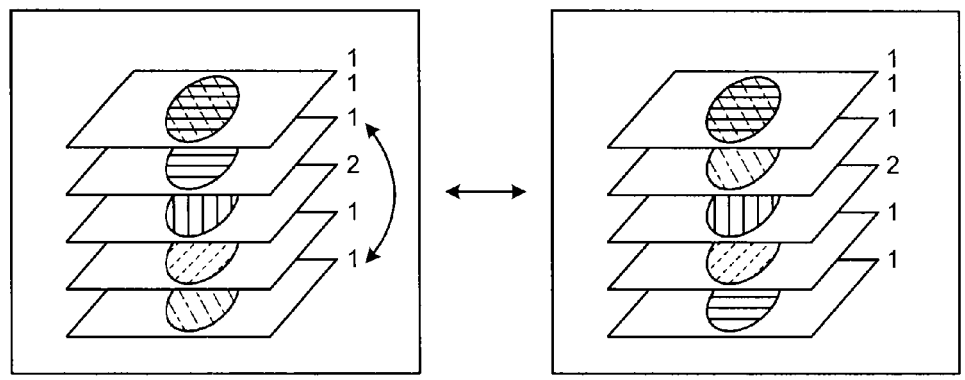
FIG. 6 illustrates a schematic diagram of a layer order changing operation according to an embodiment of the present invention.

The operation detection unit 110 may further detect a layer order changing operation, and the display unit 130 may display the plurality of medical images that are changed in layer order in the window according to the layer order changing operation. FIG. 6 illustrates a schematic diagram of a layer order changing operation according to an embodiment of the present invention. As shown in FIG. 6, in the left figure part, a layer order changing operation is performed on the first and fourth lowest layers of images in the window (as indicated by the arrow), and in the plurality of layers of images shown in the right figure part, the order of the first and fourth lowest layers of images is changed. As an example of the layer order changing operation, the sequence identifier, for example, the sequence number, of the medical image to be changed in layer order may be dragged to a desired layer position. With the layer order changing operation, the user can check an ROI in an image more clearly. Similar to the layer interval changing operation, the order of two layers of images or the order of the plurality of layers of images may be changed at a time. For instance, the plurality of layers of images may be selected in a way similar to that used in the layer interval changing operation, and then an order changing operation is performed thereon, thereby changing, for example, reversing, the order of the plurality of layers of images.

The selection of a plurality of layers of images is mentioned in both the above-described layer interval changing operation and the above-described layer order changing operation. In this case, once a plurality of layers of images are selected, a right key may be clicked for the plurality of layers of images (e.g. for the select box), and then an operation such as 'reverse order', 'increase distance' and 'shorten distance' is selected from the menu for the right key. The similar processing may be carried out in the layer rotation operation, the image hiding/display operation, the display parameter changing operation and the display content changing operation that will be described later.

Figure 7:
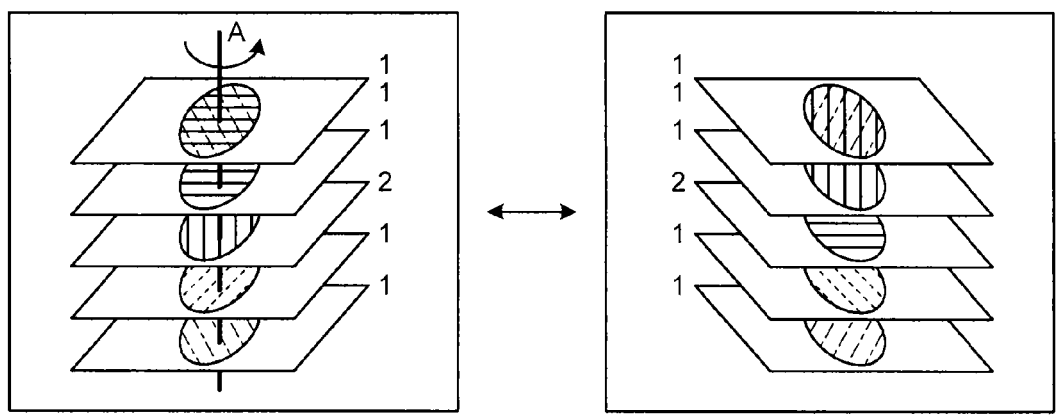
FIG. 7 illustrates a schematic diagram of a layer rotation operation according to an embodiment of the present invention.

The operation detection unit 110 may further detect a layer rotation operation, and the display unit 130 may display the layers of rotated images in the window according to the layer rotation operation. FIG. 7 illustrates a schematic diagram of a layer rotation operation according to an embodiment of the present invention. As shown in FIG. 7, in the left figure part, each layer of image is anticlockwise rotated by about 90 degree around the arrangement direction A of the images, and in the right figure part, each layer of image that is anticlockwise rotated by 90 degree is displayed in the window. As an example of the layer rotation operation, a rotational drag around the arrangement direction of the medical images (as indicated by the arc arrow shown in FIG. 7) or a rotational drag on any corner of the fused image located outside the medical images may be performed to rotate the layers of images by an angle corresponding to the magnitude of the drag. As another example of the layer rotation operation, the layer rotation operation may be triggered by inputting a predetermined hot key, such as 'Ctrl+L', to rotate the layers of images by a predetermined angle. For instance, the layers of images are clockwise or anticlockwise rotated by 90 degree around the arrangement direction of the images every time the hot key operation is operated. With the layer rotation operation, the user can check different parts of an image to check an RIO in the image more clearly, especially when the ROI in the image is sheltered.

Figure 8:
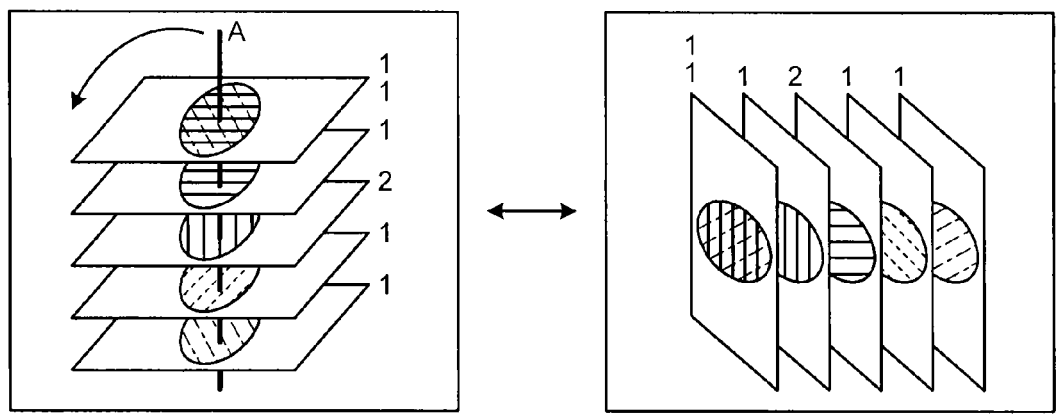
FIG. 8 illustrates a schematic diagram of an arrangement direction rotation operation according to an embodiment of the present invention.

The operation detection unit 110 may further detect an arrangement direction rotation operation, and the display unit 130 may display the layers of images of which the arrangement direction is rotated in the window according to the arrangement direction rotation operation. FIG. 8 illustrates a schematic diagram of an arrangement direction rotation operation according to an embodiment of the present invention. As shown in FIG. 8, in the left figure part, the arrangement direction A of the layers of images arranged vertically is rotated to the left by about 90 degree, and in the right figure part, the layers of images arranged horizontally resulting form the arrangement direction rotation are displayed in the window. As an example of the arrangement direction rotation operation, the arrangement direction of the layers of images may be rotated to another direction by dragging the arrangement direction of the layers of images to said another direction at a position outside the layers of images (as indicated by the arc arrow shown in FIG. 8). As another example of the arrangement direction rotation operation, the arrangement direction rotation operation may be triggered by inputting a predetermined hot key, such as 'Ctrl+R' to rotate the arrangement direction by a predetermined angle. For instance, the arrangement direction of the layers of images is clockwise or anticlockwise rotated by 90 degree every time the hot key operation is implemented. With the arrangement direction rotation operation, the user can view different parts of an image to check an ROI in the image more clearly. For instance, the arrangement direction shown in FIG. 3b can be gradually changed to the position shown in FIG. 3c. In this process, the arrangement direction can be positioned at any intermediate position.

Figure 9:
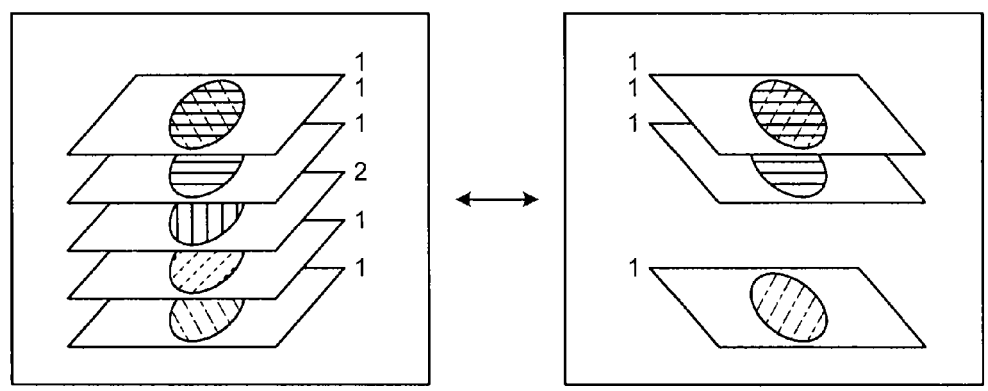
FIG. 9 illustrates a schematic diagram of an image hiding/display operation according to an embodiment of the present invention.

The operation detection unit 110 may further detect an image hiding/display operation, and the display unit 130 may hide or display parts of the plurality of medical images, for example, the medical images not participating in the fusion, the medical images participating in the fusion or a different subset of the images that are classified by any other standard, in the window according to the image hiding/display operation. FIG. 9 illustrates a schematic diagram of an image hiding/display operation according to an embodiment of the present invention. For instance, in the left part of FIG. 9, an image hiding operation is implemented in the window, and in the right part of FIG. 9, the medical images not participating in the fusion (the second and third lowest layers of images) are hidden in the window. Conversely, if an image display operation is implemented in the window in the right part of figure, then the medical images not participating in the fusion (the second and third lowest layers of images) are displayed in the window in the left part of figure. As an example of the image hiding/display operation, the image hiding operation and the image display operation may be switched by clicking a predetermined times (e.g. double click) at a predetermined position in the window. As another example of the image hiding/display operation, the image hiding operation may be triggered by inputting a predetermined hot key such as 'Ctrl+H' and the image display operation may be triggered by inputting a predetermined hot key such as 'Ctrl+D', or the image hiding operation and the image display operation may be switched by using the same predetermined hot key. With the image hiding/display operation, the images not participating in the fusion may be hidden to save the display space in the case that there are a great many medical images input.

Figure 10:
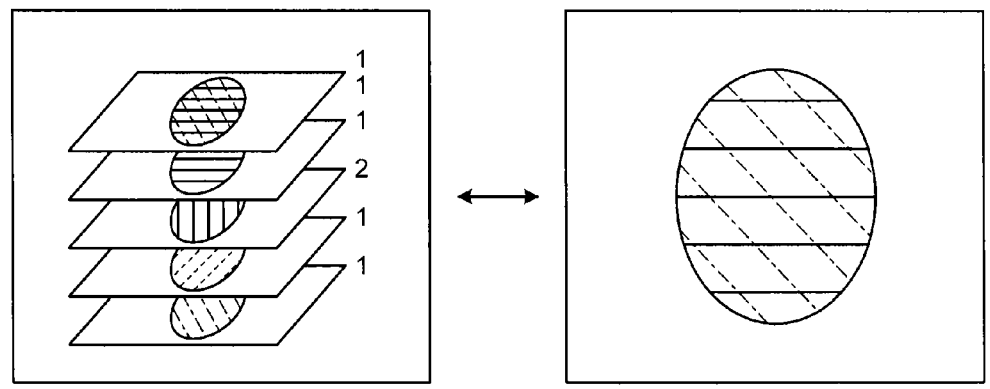
FIG. 10 illustrates a schematic diagram of a full-window switching operation according to an embodiment of the present invention.

The operation detection unit 110 may further detect a full-window switching operation, and the display unit 130 may switch the display in the window between the display of the plurality of medical images and the fused image and the full-window display of the fused image or a selected medical image. FIG. 10 illustrates a schematic diagram of a full-window switching operation according to an embodiment of the present invention. As shown in FIG. 10, through the full-window switching operation, the display of the window may be switched between the display of a plurality of medical images and a fused image as shown in the left figure part and the full-window display of the fused image or a selected medical image (the fused image in this example) as shown in the right figure part. As an example of the full-window switching operation, it may be switched to display the fused image or any one medical image in a full window, or be switched to the original display state (the display of the fused image and the plurality of medical images in the window) from the full window display state, by clicking the fused image or the medical image a predetermined times (e.g. double click). With the full window display operation, the fused or the selected medical image can be wholly viewed more clearly.

The operation detection unit 110 may further detect a display parameter changing operation of changing a display parameter of the medical images selected to be fused. The fused image generation unit 120 is further configured to re-generate a fused image using the selected medical images that are changed in display parameter. The display unit 130 is further configured to display the medical images that are changed in display parameter and the re-generated fused imaged in the window according to the display parameter changing operation. For instance, the display parameter, such as the brightness, the contrast, the transparency and the display region size of the medical images to be fused may be changed so as to change the display effect of the medical images. The display effect of the image fused by the medical images is changed correspondingly. As an example of the display parameter changing operation, the brightness of a selected medical image may be changed by adjusting a window level value displayed in the window for the selected image, the contrast of the medical image may be changed by adjusting a window width value displayed in the window, the transparency of a selected image may be changed by dragging an indicator (e.g. presented in the form of a cursor) in the transparency range (e.g. presented in the form of a bar) for the image, and the size of the display region for the image may be changed through a scale operation. The display region for an image refers to the region limited by the border of the image. When the size of the display region for an image is changed, the magnification of the image is adaptively changed so that the size of the image is adapted to the size of the display region for the image. The border or the sequence identifier (e.g. sequence number) of the image selected to be changed in display parameter may be highlighted to prompt the user that the display parameter of the image is being changed. The display parameter changing operation may be carried out for a single layer of medical image or for a plurality of layers of medical images synchronously. Alternatively, it can be set that the display parameter changing operation carried out for a single layer of medical image is synchronously applied to all other layers of medical images and/or the fused image.

The operation detection unit 110 may further detect a display content changing operation of changing the display content of a medical image selected to be fused. The fused image generation unit 120 is further configured to re-generate a fused image using the selected medical images that are changed in display content. The display unit 130 displays the medical images that are changed in display content and the re-generated fused image in the window according to the display content changing operation. For instance, the magnification of a medical image may be changed through a zoom operation, and the display unit may display the zoomed-in or zoomed-out image while the display region for the medical image is unchanged. In this manner, an ROI in the medical image can be emphatically displayed in the size-unchanged display region. For another instance, the observation position of the medical image may be changed through a pan operation, and the display unit may display the medical image that is panned in observation position in the unchanged display region for the medical image. For instance, when the magnification of the medical image is increased through a zoom operation, the medical image is partially displayed in the display region for the medical image since the zoomed-in medical image exceeds in size the display region. At this time, different parts of the zoomed-in medical image can be viewed in the size-unchanged display region through the pan operation. For another instance, the slice position of the medical image may be changed through a browse operation. It should be understood that a layer of displayed medical image may be one of a sequence of medical images. Through the browse operation (e.g. achieved by rolling the wheel of a mouse), each medical image in the sequence may be displayed one by one in the display region for the layer of image. The medical images in the same sequence are located at different slice positions. Images at different slice positions can be viewed through a slice position changing operation. The display content changing operation may be carried out for a single layer of medical image or for the plurality of layers of medical images synchronously. Alternatively, it can be set that the display content changing operation carried out for a single layer of medical image is synchronously applied to all other layers of medical images and/or the fused image.

The operation detection unit 110 may detect a synchronous activation or cancelling operation. The display unit may activate or cancel the synchronous display, including the synchronous display of display parameter changing and the synchronous display of display content changing, of at least two layers of medical images according to the synchronous activation or cancelling operation. Especially, in view of the image fusion purpose of the present invention, when the slice position of one layer of medical image is changed, the slice positions of the other layers of medical images, especially, the medical images participating in the fusion, must be synchronously changed. However, as medical images of different layers belong to different modalities or different sequences, the slice positions of the layers of medical images that are synchronously changed may not correspond to each other exactly. At this time, the synchronization should be disabled and the slice position of each layer of medical image needs to be fine-tuned one by one (or the slice positions of multiple layers of medical images may be fine-tuned at a time).

Figure 11:
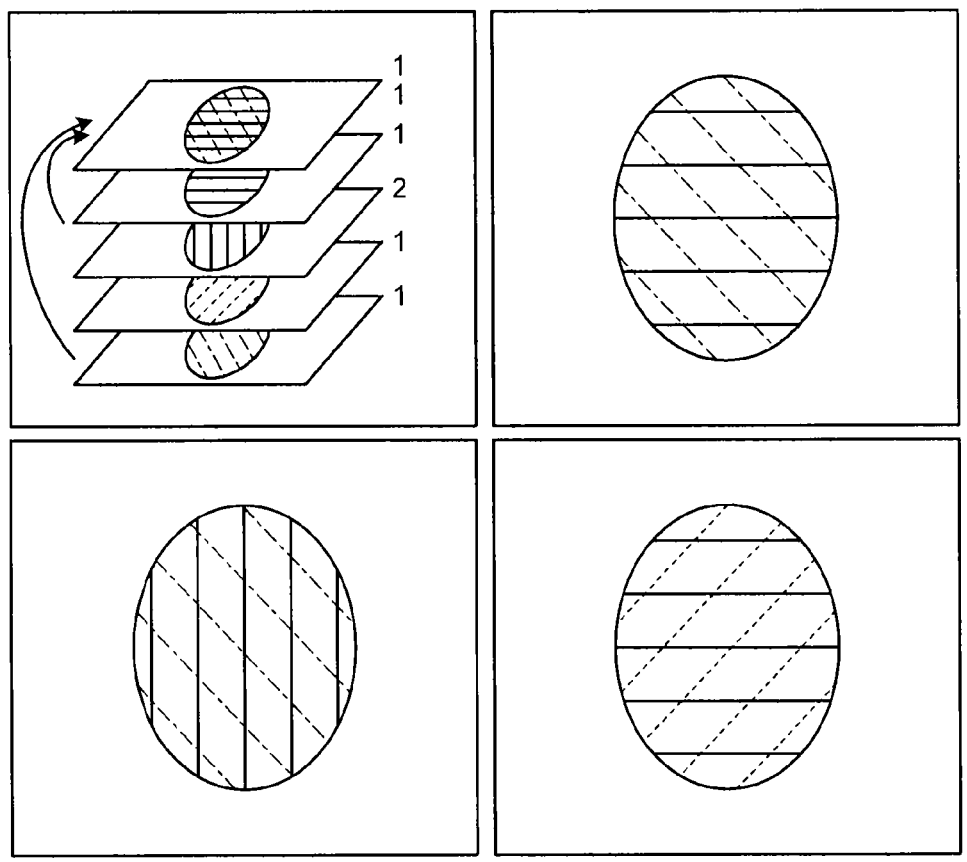
FIG. 11 illustrates a schematic diagram of a transfer operation according to an embodiment of the present invention.

The operation detection unit 110 may further detect, on a screen, a transfer operation of putting the generated fused image into another window. The display unit 130 may further display one or more generated fused images in one or more other windows on the screen according to the transfer operation. FIG. 11 illustrates a schematic diagram of a transfer operation according to an embodiment of the present invention. As shown in FIG. 11, with the transfer operation, the fused images generated are displayed in the right upper window, the left lower window and the left upper window, respectively. As an example of the transfer operation, the fused image displayed in the window in which the fused image and the plurality of medical images are displayed may be dragged to another window for display. With the transfer operation, different fused images may be synchronously displayed in a plurality of windows so as to compare different fused images. In addition, various operations may be carried out for the fused image in another window without influencing the medical images shown in the original window for forming the fused image. Besides, the transfer operation may copy the medical images participating in the fusion together with the fused image into said another window. Similarly, the operation detection unit 110 may further detect a second full-window switching operation carried out for the another window, and the display unit 130 may further switch the display in the another window between the full window display of the generated fused image and the display of the medical images participating in the fusion of the fused image and the generated fused image in the another window according to the second full-window switching operation. The window currently to be operated may be selected in any appropriate may. It should be understood that a layer order changing operation, a layer interval changing operation, a layer rotation operation, an arrangement direction rotation operation, a display parameter changing operation and a display content changing operation that are applicable to the another window may be set to enable the operation detection unit 110 to detect any one of the above-mentioned operations on the another window and enable the display unit 130 to change the display in the another window accordingly according to the operation detected. The detection of the above-mentioned operations on another window and a corresponding change in the display of image(s) are substantially identical to those implemented for the original window and are therefore not repeated here.

Similarly, the aforementioned layer order changing operation, layer interval changing operation, layer rotation operation, arrangement direction rotation operation, image hiding/display operation, full-window switching operation, display parameter changing operation and display content changing operation may also be achieved by manipulating a cursor on a screen with a mouse or through a slide or click on a touch screen with a finger. The operation detection unit 110 may detect the aforementioned operations on the screen or input through a physical keyboard using any appropriate existing technology, which will not be described in detail here. Additionally, when some or all of the aforementioned operations are triggered using hot keys, the operation detection unit 110 may detect the hot keys input through a keyboard (e.g. a physical keyboard or a soft keyboard on a screen) using any appropriate existing technology, which will not be described in detail here.

Based on the above description, those skilled in the art may devise more other operations to implement more other appropriate processing on the medical images and the fused image displayed in the window, which will not be listed here.

FIG. 2 illustrates a schematic flowchart of a medical image fusion method according to an embodiment of the present invention. As shown in FIG. 2, in Step S210, a plurality of medical images are displayed in layers in a window on a screen, wherein the arrangement direction of the plurality of medical images is different from the extension direction of the plane on which each medical image exists. In Step S220, an operation of selecting the medical images to be fused from the plurality of medical images is detected. In Step S230, the fused image of the medical images to be fused is generated according to the selection operation. In Step S240, the fused image is displayed in the predetermined region in the window. In the method, Steps S210 and S240 may be carried out by the display unit 130 of the medical image display apparatus 100 according to the embodiments of the present invention, Steps S220 may be carried out by the operation detection unit 110, and S230 may be carried out by the fused image generation unit 120. More specific details of each step of the medical image fusion method may be understood with reference to the description on each component of the medical image display apparatus according to the embodiments of the present invention and therefore will not be repeated here.

In the medical image display apparatus and method according to the embodiments of the present invention, a plurality of medical images and a fused image are synchronously displayed in the same window to save window resource. The display of the plurality of medical images in layers enables the medical images to be operated synchronously.

As an example, the respective steps of the above-described medical image fusion method and the respective sections, modules and/or units of the above-described medical image display apparatus may be implemented as software, firmware, hardware or the combination thereof in a medical diagnostic apparatus (e.g. X-ray diagnostic device, UL diagnostic device, CT device, MRI diagnostic device or PET device), and serve as a part of the medical diagnostic apparatus. As an example, the above-described method and/or apparatus may be implemented in an existing medical diagnostic device by making some modification on the sections of the existing medical diagnostic device. As another example, the respective steps of the above-described method and the respective sections, modules and/or units of the above-described apparatus may be implemented as an apparatus separately from the above-described medical diagnostic apparatus. The specific means or approaches that may be used in configuring the sections, modules and units in the foregoing medical image display apparatus through software, firmware, hardware or any combination thereof are well known to those skilled in the art and therefore will not be repeatedly described.

As an example, the steps of the above-described method and the sections, modules and/or units of the above-described apparatus may be implemented as software, firmware, hardware or any combination thereof. In the case where the steps of the above-described method and the sections, modules and/or units of the above-described apparatus are implemented through software or firmware, a software program constituting the software for realizing the above-described methods may be installed in a computer (e.g. the general computer 1200 shown in FIG. 12) with a specific hardware structure from a storage medium or a network, and the computer, when installed with various programs, is capable of perform various functions.

Figure 12:
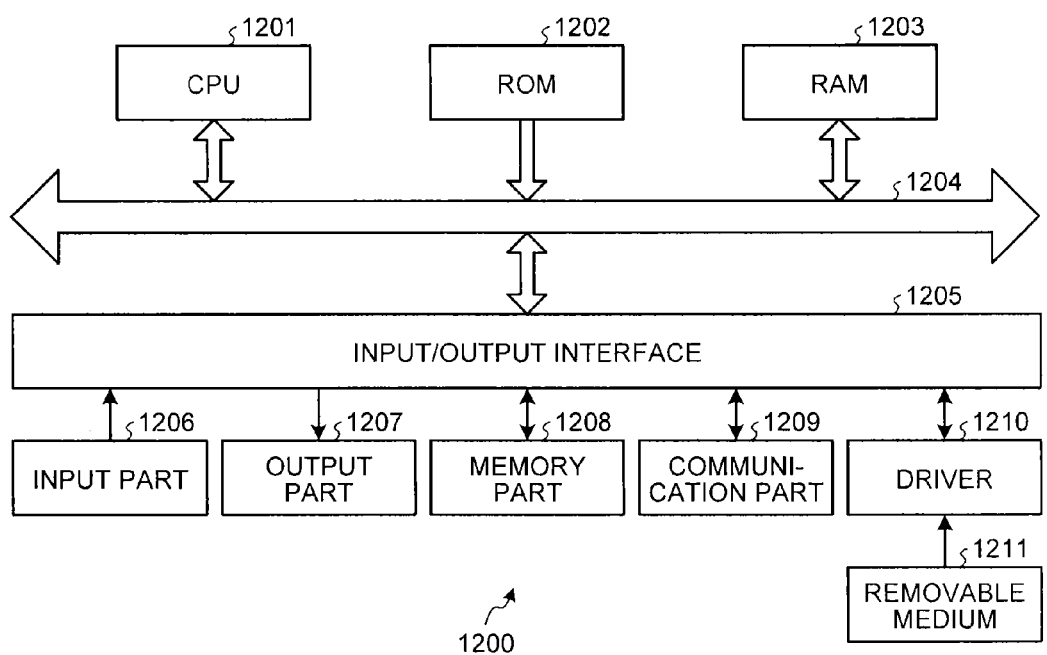
FIG. 12 shows a computer structure capable of realizing the method/apparatus provided in embodiments of the present invention.

In FIG. 12, a central processing unit (i.e. CPU) 1201 executes various processes according to the programs stored in a read-only memory (ROM) 1202 or programs loaded to a random access memory (RAM) 1203 from a storage part 1208. Data needed by the CPU 1201 in executing the various processes are also stored in the RAM 1203 as required. The CPU 1201, the ROM 1202 and the RAM 1203 are connected with each other via a bus 1204. An input/output interface 1205 is also connected to the bus 1204.

The following parts are connected to the input/output (I/O) interface 1205: an input part 1206 (including a keyboard, a mouse and etc.), an output part 1207 (including a display such as a cathode-ray tube (CRT) or a liquid crystal display (LCD), and a speaker, etc.), the storage part 1208 (including a hard disk, etc.), and a communication part 1209 (including a network interface card such as an LAN card, a MODEM and etc.). The communication part 1209 executes communication processing via a network such as the Internet. A driver 1210 can also be connected to the input/output interface 1205 as required. A removable medium 1211 such as a magnetic disk, an optical disk, a magneto-optical disk or a semiconductor memory can be mounted on the driver 1210 as required, such that the computer program read out therefrom is installed into the storage part 1208 as required.

In the case that the above series of processes are implemented by software, a program constituting the software is installed from a network such as the Internet or from a storage medium such as the removable medium 1211.

It is to be understood by those skilled in the art that such storage medium is not limited to the removable medium 1211 storing programs therein and distributing the programs to a user(s) dependently from a device. Examples of the removable medium 1211 include a magnetic disk (including a Floppy Disk (registered trademark)), an optical disk (including a Compact Disk-Read Only Memory (CD-ROM) and a Digital Versatile Disc (DVD)), a magneto-optical disk (including a Microdisk (MD) (registered trademark)) and a semiconductor memory. Alternatively, the storage medium can be the ROM 1202, a hard disk contained in the storage part 1208, etc., in which programs are stored and which is distributed to a user(s) along with a device the storage medium is contained in.

The present invention further provides a program product in which computer-readable instruction codes are stored. The instruction codes, when read and executed by a machine, can execute the method according to the embodiments of the present invention.

Correspondingly, the storage medium for carrying the program product storing machine-readable instruction codes is also incorporated in the disclosure of the present invention. The storage medium includes, but is not limited to, a flexible disk, an optical disk, a magneto-optical disk, a storage card and a storage stick.

In the above description of the specific embodiments of the present invention, features described and/or illustrated with respect to one embodiment can be used in one or more other embodiments in an identical or similar manner, be combined with features in other embodiments, or replace features in other embodiments.

It should be emphasized that, the term "comprise/include", as used in the present description, refers to the presence of features, sections, steps or components, but does not exclude the presence or addition of one or more other features, sections, steps or components.

In the above embodiments and examples, the steps and/or units are represented with a reference sign consisting of numbers. It should be understood by those of ordinary skill of the art that the reference signs are merely intended to facilitate description and drawing depiction, but are not to be construed as indicating the orders of the steps and/or units nor a limitation on any other aspect.

Furthermore, the methods of the present invention are not limited to being executed in the temporal orders as described in the specification, but can also be executed in other temporal order, in parallel or separately. Therefore, the execution orders of the methods described in the present specification do not constitute a limitation to the technical scope of the present invention.

Although the present invention has been disclosed with reference to descriptions for the specific embodiments of the present invention, it should be understood that all of the above mentioned embodiments and examples are illustrative instead of limiting. Those skilled in the art can devise various modifications, improvements or equivalents for the present invention, within the spirit and scope of the appended claims. The modifications, improvements or equivalents should also be considered as being included in the protection scope of the present invention.

Contents (1)-(18) are disclosed below.

(1) A medical image fusion apparatus, comprising:
a display unit configured to display a plurality of medical images in layers in one window on a screen, wherein the arrangement direction of the plurality of medical images is different from the extension direction of the plane on which each medical image exists;
an operation detection unit configured to detect a selection operation of selecting the medical images to be fused from the plurality of medical images; and
a fused image generation unit configured to generate a fused image of the medical images to be fused according to the selection operation,
wherein the display unit is further configured to display the fused image in a predetermined region in the window.

(2) The medical image fusion apparatus according to the above (1), wherein the predetermined region is arranged outside the outmost layer of medical image of the plurality of medical images.

(3) The medical image fusion apparatus according to the above (1), wherein the selection operation comprises associating the medical images to be fused with the predetermined region.

(4) The medical image fusion apparatus according to the above (3), wherein the selection operation comprises dragging the medical images to be fused into the predetermined region.

(5) The medical image fusion apparatus according to the above (1), wherein the plurality of medical images are medical images of different modalities and/or different sequences, and the display unit distinguishes, in the window, the medical images of different modalities with a first kind of identifiers and the medical images of different sequences with a second kind of identifiers.

(6) The medical image fusion apparatus according to the above (5), wherein the display unit identifies the fused image with a combination of the identifiers of the medical images to be fused.

(7) The medical image fusion apparatus according to the above (5), wherein the medical images of different modalities are distinguished from each other with a border color, and the medical images of the same modality in different sequences are distinguished from each other with a sequence number.

(8) The medical image fusion apparatus according to the above (7), wherein the selection operation comprises associating the medical images to be fused with the predetermined region by operating the sequence numbers of the medical images to be fused.

(9) The medical image fusion apparatus according to the above (1), wherein the fused image generation unit generates the fused image by overlapping the medical images to be used according to a selection order of the selection operation.

(10) The medical image fusion apparatus according to the above (1), wherein the operation detection unit is also configured to detect one of the following operations: a layer order changing operation, a layer interval changing operation, a layer rotation operation, an arrangement direction rotation operation, an image hiding/display operation, a full-window switching operation and a fusion cancelling operation; and the display unit is further configured to change the display in the window according to the operation detected by the operation detection unit, including:

displaying, according to the layer order changing operation, the plurality of medical images that are changed in layer order in the window;

displaying, according to the layer interval changing operation, the images two or more layers of which are changed in layer interval in the window;

displaying the layers of images that are rotated in the window according to the layer rotation operation;

displaying, according to the arrangement direction rotation operation, the layers of images of which the arrangement direction is rotated in the window;

displaying or hiding, according to the image hiding/display operation, the ones of the plurality of medical images not participating in the fusion in the window; switching the display in the window between the display of the plurality of medical images and the fused image and the full-window display of the fused image or a selected medical image according to the full-window switching operation; or canceling the display of the fused image according to the fusion cancelling operation.

(11) The medical image fusion apparatus according to the above (10), wherein the fusion cancelling operation comprises moving the fused image outside the predetermined region.

(12) The medical image fusion apparatus according to the above (1), wherein the operation detection unit is further configured to detect a display parameter changing operation of changing a display parameter of the medical images selected to be fused, the fused image generation unit is further configured to re-generate the fused image by using the selected medical images that are changed in display parameter, and the display unit is further configured to display the medical images that are changed in display parameter and the re-generated fused imaged in the window according to the display parameter changing operation.

(13) The medical image fusion apparatus according to the above (1), wherein the operation detection unit is further configured to detect a display content changing operation of changing a display content of the medical images selected to be fused, the fused image generation unit is further configured to re-generate the fused image by using the selected medical images that are changed in display content, and the display unit is further configured to display the medical images that are changed in display content and the re-generated fused imaged in the window according to the display content changing operation.

(14) The medical image fusion apparatus according to the above (12) or (13), wherein the operation detection unit is further configured to detect a synchronous activation or cancelling operation, and the display unit is further configured to activate or cancel the synchronous display of at least two layers of medical images according to the synchronous activation or cancelling operation.

(15) The medical image fusion apparatus according to the above (1), wherein the display unit displays the plurality of medical images and the fused image as three-dimensional images.

(16) The medical image fusion apparatus according to the above (1), wherein the operation detection unit is further configured to detect a transfer operation of putting the generated fused image into another window, and the display unit is further configured to display one or more generated fused images in one or more other windows on the screen.

(17) The medical image fusion apparatus according to the above (16), wherein the transfer operation is further configured to copy the medical images participating in the fusion of the generated fused image to the another window, the operation detection unit is further configured to detect a second full-window switching operation, and the display unit is further configured to switch the display in the another window between the full-window display of the generated fused image and the display of the medical images participating in the fusion of the generated fused image and the generated fused image in the another window according to the second full-window switching operation.

(18) The medical image fusion apparatus according to the above (1), wherein the medical images in adjacent layers are at least partially overlapped.

(19) A medical image fusion method, comprising:

displaying a plurality of medical images in layers in one window on a screen, wherein the arrangement direction of the plurality of medical images is different from the extension direction of the plane on which each medical image exists;

detecting a selection operation of selecting the medical images to be fused from the plurality of medical images;

generating a fused image of the medical images to be fused according to the selection operation; and displaying the fused image in a predetermined region in the window.

What is claimed is:

1. A medical image display apparatus, comprising:
processing circuitry configured to
cause a first display region on a display to display a plurality of modified medical images that are generated by reducing a length, in a predetermined direction of the first display region, of a plurality of medical images of substantially an identical region of a subject, wherein partial areas of the modified medical images overlap with each other in such a manner as to arrange the modified medical images in the predetermined direction;

detect a selection operation to select at least two of the displayed modified medical images to be fused, from the plurality of modified medical images; and generate a fused image from the at least two medical images corresponding to the at least two selected modified medical images selected by the selection operation, wherein the processing circuitry is further configured to cause the fused image to be displayed in a second display region on the display, which is different from the first display region on the display.

2. The medical image display apparatus according to claim 1, wherein the processing circuitry is further configured to cause the display to display the fused image in the first display region, wherein a partial area of the fused image is overlapped with at least one of the plurality of modified medical images.

3. The medical image display apparatus according to claim 2, wherein the processing circuitry is further configured to cause the display to display the fused image in the foreground in the first display region.

4. The medical image display apparatus according to claim 1, wherein the processing circuitry is further configured to cause the display to display the fused image and the modified medial images corresponding to the medical images from which the fused image is generated, wherein both of the fused image and the medical images are each displayed with an identical identifier.

5. The medical image display apparatus according to claim 1, wherein the processing circuitry is further configured to detect a cancelling operation to cancel a display of the fused image in the second display region, and cancel the display of the fused image when the cancelling operation is detected.

6. The medical image display apparatus according to claim 5, wherein the processing circuitry is further configured to detect a drag-and-drop operation to move the fused image out of the second display region as the cancelling operation.

7. The medical image display apparatus according to claim 1, wherein the processing circuitry is further configured to detect a layer interval changing operation to change an interval between two layers of a plurality of layers of the modified medical images displayed in the first display region, and cause the display to display in the first display region the two layers of the modified medical images at the interval changed by the layer interval changing operation when the layer interval changing operation is detected.

8. The medical image display apparatus according to claim 1, wherein the processing circuitry is further configured to detect an order changing operation to change an order of the plurality of modified medical images displayed in the first display region, and cause the display to display in the first display region the plurality of modified medical images in the order when the order changing operation is detected.

9. The medical image display apparatus according to claim 1, wherein the processing circuitry is further configured to detect a layer rotation operation to rotate layers of the plurality of the modified medical images displayed in the first display region, and cause the display to display in the first display region the layers of the plurality of the modified medical images rotated by the layer rotation operation.

10. The medical image display apparatus according to claim 1, wherein the processing circuitry is further configured to detect an arrangement direction rotation operation to rotate an arrangement direction of the plurality of the modified medical images displayed in the first display region, and cause the display to display in the first display region the plurality of the modified medical images of which the arrangement direction is rotated by the arrangement direction rotation operation.

11. The medical image display apparatus according to claim 1, wherein the processing circuitry is further configured to detect a display changing operation regarding a modified medical image of the plurality of modified medical images, and cause the display to hide the modified medical image when the modified medical image is displayed in the first display region when the display changing operation is detected, and display the modified medical image when the modified medical image is not displayed in the first display region when the display changing operation is detected.

12. The medical image display apparatus according to claim 1, wherein the processing circuitry is further configured to detect any one of a first display operation to display the first display region on a full-window of the screen, a second display operation to display the second display region on the full-window, and a third display operation to display the first display region and the second display region on the full-window, and cause the display to display the first display region on the full-window when the first display operation is detected, display the second display region on the full-window when the second display operation is detected, and display the first display region and the second display region on the full-window when the third display operation is detected.

13. The medical image display apparatus according to claim 1, wherein the processing circuitry is further configured to detect a display parameter changing operation to change a display parameter of a medical image of the plurality of the medical images, the display parameter including at least one of brightness, contrast, transparency, and display region size of the medical images to be fused, and re-generate the fused image by using the medical image of which the display parameter is changed.

14. The medical image display apparatus according to claim 1, wherein the processing circuitry is further configured to detect a selection operation to generate at least two different fused images, generate the at least two different fused images when the selection operation is detected, and cause the display to display the generated at least two different fused images on different display regions, respectively.

15. A medical image display method executed by a medical image display apparatus, the method comprising:
   causing a first display region on a display to display a plurality of modified medical images that are generated by reducing a length, in a predetermined direction of the first display region, of a plurality of medical images of substantially an identical region of a subject, wherein partial areas of the modified medical images overlap with each other in such a manner as to arrange the plurality of modified medical images in the predetermined direction;
   detecting, using the medical image display apparatus, a selection operation to select the at least two of the displayed modified medical images to be fused, from the plurality of modified medical images; and
   generating, using the medical image display apparatus, a fused image from the at least two medical images corresponding to the at least two selected modified medical images selected by the selection operation,
   wherein the causing step further comprises causing the fused image to be displayed in a second display region different from the first display region on the display.

16. The medical image display apparatus of claim 1, wherein the processing circuitry is configured to cause the display to display the plurality of modified medical images so that a portion of each of the plurality of modified medical images is not covered by any of the other medical images.

\* \* \* \* \*